(12) United States Patent
Hill et al.

(10) Patent No.: US 6,827,737 B2
(45) Date of Patent: Dec. 7, 2004

(54) EPTFE COVERING FOR ENDOVASCULAR PROSTHESES AND METHOD OF MANUFACTURE

(75) Inventors: Jason Peter Hill, Brooklyn Park, MN (US); David John Sogard, Edina, MN (US); David Tseng, Santa Rosa, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 138 days.

(21) Appl. No.: 09/962,062

(22) Filed: Sep. 25, 2001

(65) Prior Publication Data

US 2003/0060871 A1 Mar. 27, 2003

(51) Int. Cl.$^7$ .............................................. A61B 17/00
(52) U.S. Cl. ...................................... 623/1.4; 623/1.13
(58) Field of Search .............................. 606/191, 192, 606/194, 198; 623/1.12, 1.13, 1.14, 1.15, 1.23, 1.36, 1.38, 1.39, 1.4, 1.42, 1.43, 1.44, 1.45, 1.46, 1.47, 1.48

(56) References Cited

U.S. PATENT DOCUMENTS

| 4,478,898 A | | 10/1984 | Kato |
| 4,816,339 A | | 3/1989 | Tu et al. |
| 4,955,899 A | * | 9/1990 | Della Corna et al. ...... 623/1.46 |
| 5,001,276 A | | 3/1991 | Klaus et al. |
| 5,197,977 A | * | 3/1993 | Hoffman et al. ........... 623/1.39 |

(List continued on next page.)

FOREIGN PATENT DOCUMENTS

| WO | WO 91/12779 | 9/1991 |
| WO | WO 99/47077 | 9/1999 |

OTHER PUBLICATIONS

Katami, K., et al.; Healing Characteristics of Bilayer ePTFE Vascular Graft Composed of High Porosity Inner Layer and Low Porosity Outer Layer; Japanese Journal of Artificial Organs, vol. 25, No. 2, 1996, pp. 455–459.

Nagae, T., et al.; Enhanced neointima formation and attachment on the high–porosity inner surface of modified PTFE vascular grafts; Journal of Investigative Surgery: The Official Journal of the Academy of Surgical Research, U.S., Jul–Aug. 1995; vol. 8, No. 4, Jul. 1995, pp. 235–242.

Nagae, T., et al.; Composite porosity of expanded polytetrafluoroethylene vascular prosthesis; Cardiovascular Surgery, London, England, vol. 3 No. 5; Oct. 1995, pp. 479–484.

Soldani, G. and Mercogliano, R., "Bioartificial polymeric materials obtained from blends of synthetic polymers with fibrin and collagen", International Journal of Artificial Organs/vol. 14/No. 5 1991/ pp. 295–303.

*Primary Examiner*—Julian W. Woo
*Assistant Examiner*—Jessica R. Baxter
(74) *Attorney, Agent, or Firm*—Mayer Fortkort & Williams, PC; David B. Bonham, Esq.

(57) ABSTRACT

An implantable composite device for regulated delivery of bioactive agents to the site of implantation includes at least two zones of distinct porosities through its cross-section. One zone is of a sufficient porosity to permit regulated transport of bioactive agents associated with the device to an area of the body in need of treatment. The bioactive agent associated with the device can be either a therapeutic or diagnostic agent. In a particular embodiment of the invention, the device includes a tubular body consisting of a first luminal layer of ePTFE having a porosity sufficient to promote cell endothelization along the luminal surface; and a second polymeric layer disposed on the first layer of a porosity permitting regulated transport of the bioactive agents.

49 Claims, 5 Drawing Sheets

U.S. PATENT DOCUMENTS

| | | | | |
|---|---|---|---|---|
| 5,229,045 A | * | 7/1993 | Soldani | 623/921 |
| 5,290,271 A | | 3/1994 | Jernberg | |
| 5,316,023 A | * | 5/1994 | Palmaz et al. | 606/198 |
| 5,370,681 A | * | 12/1994 | Herweck et al. | 623/1.39 |
| 5,399,352 A | * | 3/1995 | Hanson | 623/1.42 |
| 5,411,550 A | | 5/1995 | Herweck et al. | |
| 5,429,634 A | * | 7/1995 | Narciso, Jr. | 604/890.1 |
| 5,433,909 A | | 7/1995 | Martakos et al. | |
| 5,474,824 A | | 12/1995 | Martakos et al. | |
| 5,591,224 A | | 1/1997 | Schwartz et al. | |
| 5,628,782 A | * | 5/1997 | Myers et al. | 623/2.25 |
| 5,665,114 A | | 9/1997 | Weadock et al. | |
| 5,674,241 A | * | 10/1997 | Bley et al. | 606/198 |
| 5,674,242 A | * | 10/1997 | Phan et al. | 606/198 |
| 5,693,085 A | * | 12/1997 | Buirge et al. | 606/194 |
| 5,749,880 A | | 5/1998 | Banas et al. | |
| 5,788,626 A | | 8/1998 | Thompson | |
| 5,800,512 A | | 9/1998 | Lentz et al. | |
| 5,810,870 A | | 9/1998 | Myers et al. | |
| 5,824,049 A | * | 10/1998 | Ragheb et al. | 623/1.44 |
| 5,824,050 A | | 10/1998 | Karwoski | |
| 5,897,587 A | | 4/1999 | Martakos et al. | |
| 5,935,667 A | | 8/1999 | Calcote et al. | |
| 6,071,305 A | | 6/2000 | Brown et al. | |
| 6,120,535 A | * | 9/2000 | McDonald et al. | 623/1.39 |

* cited by examiner

EPTFE COVERING FOR ENDOVASCULAR PROSTHESES AND METHOD OF MANUFACTURE

FIELD OF THE INVENTION

The present invention relates generally to a tubular implantable prosthesis for the delivery of a bioactive material. More particularly, the present invention relates to a multi-layered tubular endoprosthesis formed of a combination of expanded polytetrafluoroethylene, and a tubular, diametrically-deformable stent.

BACKGROUND OF THE INVENTION

It is known to use extruded tubes of polytetrafluoroethylene (PTFE) as implantable intraluminal prosthesis, particularly vascular grafts, stents, and stent/graft composites. PTFE is particularly suitable as an implantable prosthesis due to its biocompatibility. PTFE tubes may be used as vascular grafts in the replacement or repair of blood vessels. In vascular applications, the grafts, stents, and stent/graft composites are manufactured from expanded polytetrafluoroethylene (ePTFE) tubes. Extruded PTFE tubes having minimal wall thickness are described in commonly owned, copending application Ser. No. 10/012,919. An apparatus and method for extrusion of thin-walled PTFE tubes are described in commonly owned, copending application Ser. No. 10/012,825.

Grafts formed of ePTFE have a fibrous state which is characterized by lengthwise-oriented fibrils interrupted by transverse nodes, the fibrous state being formed during the process of stretching and expanding the PTFE. The space between the node surfaces that is spanned by the fibrils is defined as the internodal distance (IND). Nodes and fibrils may be further characterized in terms of their relative geometry. In particular, nodes can be characterized by length, width, and height; and fibrils, by diameter and length. It is the relative geometry of nodes to fibrils, as well as the internodal distance that determines the porosity and permeability of porous PTFE.

The porosity of an ePTFE vascular graft may be tailored to achieve desirable properties in the structures of nodes and fibrils that affect cell permeability and tissue in-growth. For example, by controlling the conditions under which PTFE is stretched and expanded, the IND of the microporous structure of the tube can be varied. It is known that a graft having a large IND, for example, greater than 30 microns, results in enhanced tissue growth as well as cell endothelization as a result of the graft being inherently more porous. However, such an increase in the porosity of the tubular structure also results in a reduction in the overall radial tensile strength of the tube as well as a reduction in the ability of the graft to retain a suture placed during implantation. In addition, microporous tubular structures having a large IND tend to exhibit low axial tear strength, so that a small tear or nick will tend to propagate along the length of the tube.

Attempts to increase the radial tensile and axial tear strengths of microporous ePTFE tubes include forming the tubular grafts of multiple layers placed over one another. Examples of multi-layered ePTFE tubular structures useful as implantable prosthesis are shown in U.S. Pat. Nos. 4,816,339; 4,478,898; 5,001,276; 5,800,512; 5,749,880; 5,810,870; and 5,824,050.

It is further known to provide a tubular vascular graft of ePTFE with layers sufficient to provide a differential cross-section of permeability and/or porosity to achieve enhanced healing and tissue in-growth. For example, U.S. Pat. No. 5,800,512 describes a multi-layered ePTFE composite tubular structure including a tissue contacting expanded outer tube and a concentrically adjacent expanded inner tube, an inner surface of which is a blood contacting surface. The graft has an inner tube with an IND of greater than 40 microns which promotes cell endothelization along the inner surface and an outer tube of ePTFE having an IND of less than 40 microns which exhibits an increased radial strength relative to the inner tube. A middle layer of ePTFE of low IND may be interposed for increasing the radial strength of the resultant composite graft. Alternately, a middle layer of high IND may be interposed for increasing the porosity of the composite structure for further promoting cell endothelization and/or tissue in-growth.

Moreover, U.S. Pat. No. 5,824,050 discloses a multi-layered tubular graft, which may be formed of layers of ePTFE, having different porosities. A three layer graft includes three cross-section regions wherein the IND of the pores of the luminal surface of the graft is about 20 or 30 microns and the tissue contacting surface of the graft has a pore size range of 50 to 500 microns. A middle layer of low IND modulates cellular penetration between the outer and inner layers, while allowing the transport of plasma solutes between the outer and inner layers. The barrier middle layer minimizes the relatively large hydraulic force present in arterial transport that retards tissue growth. A disadvantage of this tubular graft is that the outer layer, because of its large IND, exhibits a decreased radial strength. Thus, this graft may not be suitable for use in combination with an expandable device, such as a balloon-expandable stent.

It is also known to incorporate therapeutic agents into implantable ePTFE materials. The use of therapeutic agents in ePTFE prosthetics is desirable to prevent various complications which may arise as a result of implantation of the prosthetic and to promote cell endothelization, tissue in-growth and healing. Such therapeutic agents can be provided in the ePTFE material as a dispersion in a biocompatible, biodegradable material. Various pharmacological active agents, such as antimicrobials, antivirals, antibiotics, growth factors, and blood clotting modulators, such as heparin, can be added to the material such that these agents are introduced into the body as the material is bioresorbed. For example, U.S. Pat. No. 5,665,114 to Weadock et al. discloses an implantable ePTFE prosthesis which incorporates a biocompatible, biodegradable material of natural origin.

U.S. Pat. No. 5,411,550 also describes an implantable prosthetic device for delivering a bioactive material into a blood vessel of a patient. The device including a single tubular body of ePTFE extruded as a continuous wall, the wall having at least a primary and secondary lumen, wherein the secondary lumen receives the bioactive material. A disadvantage of this device is that because the tubular body is extruded as a single continuous wall, it is not possible to provide a luminal surface and a tissue contacting surface with distinct porosities.

There is, therefore, a need to provide ePTFE multi-layered tubular grafts and stent/graft configurations which exhibit increased porosity, desirably at the inner surface thereof, while retaining a high degree of radial strength, desirably at the external surface thereof and which provide for regulated delivery of therapeutic agents incorporated therein or thereon to a site of implantation of the device. In particular, it is desirable to provide an ePTFE vascular graft and stent/graft configuration which includes a mechanism for regulating the transport of substances between surfaces of the prosthesis with a high degree of specificity.

SUMMARY OF THE INVENTION

The present invention provides for an implantable composite device for regulating delivery of bioactive agents associated therewith to a site of implantation of the device including: (a) a luminal zone of first porosity; and (b) a second zone of second porosity circumscribing the luminal zone, the second zone permitting regulated transport of natural or synthetic bioactive agents therethrough.

The invention further provides for an implantable composite device for regulating delivery of bioactive agents associated therewith to a site of implantation of the device including (a) a first luminal layer of ePTFE having a first porosity sufficient to promote cell endothelization thereal-ong; and (b) a second polymeric layer disposed on the first layer, the second layer having a second porosity permitting regulated transport of natural or synthetic bioactive therapeutic agents therethrough.

In one embodiment of the present invention, the implantable composite device for regulating delivery of bioactive agents associated therewith to a site of implantation of the device includes: (a) a first luminal layer of ePTFE having pores of an internodal distance of greater than 40 microns and (b) a second layer disposed on the first layer, the second layer having a porosity defined by an internodal distance of about 5–10 microns and a specific node/fibril geometry of about 5 to about 10 microns, the second layer permitting regulated transport of natural or synthetic bioactive therapeutic agents therethrough.

In a further embodiment, the implantable composite device for regulating delivery of bioactive agents associated therewith to a site of implantation of the device includes: (a) a first luminal layer of ePTFE having pores of an internodal distance of less than 40 microns and (b) a second layer of ePTFE disposed on the first layer, the second layer having a porosity defined by an internodal distance of about 5–10 microns and a specific node/fibril geometry of about 5 to about 10 microns, the second layer permitting regulated transport of natural or synthetic bioactive therapeutic agents therethrough.

In another aspect of the invention there is provided a method of making an implantable composite device for regulating delivery of bioactive agents associated therewith to a site of implantation of the device, the method including: (a) providing a first luminal layer of ePTFE material of a first porosity and (b) disposing a second layer of a natural or synthetic polymeric material of a second porosity onto the first layer, the second layer permitting regulated transport of natural or synthetic bioactive agents therethrough.

Furthermore, a method for treating a lumen in a body is provided, the method including the steps of: (a) inserting an implantable composite device for regulating delivery of bioactive agents associated therewith into said lumen, the device including : (i) a luminal zone of first porosity; and (ii) a second zone of second porosity circumscribing the luminal zone, the second zone permitting regulated transport of natural or synthetic bioactive agents therethrough; and (b) fixing said implantable composite device to said lumen such that it will stay where positioned.

DETAILED DESCRIPTION OF THE INVENTION

In preferred embodiments of the present invention, the implantable composite device is a multi-layered tubular structure which is particularly suited for use as an endoprosthesis or vascular graft. The prosthesis includes at least one extruded polytetrafluoroethylene (PTFE) tube as PTFE exhibits superior biocompatibility and is suitable for vascular applications as a result of its low thrombogenicity. Furthermore, the prosthesis includes a second tube of a polymeric material designed to regulate delivery of a drug associated with the prosthesis to the site of implantation.

Figure 1:
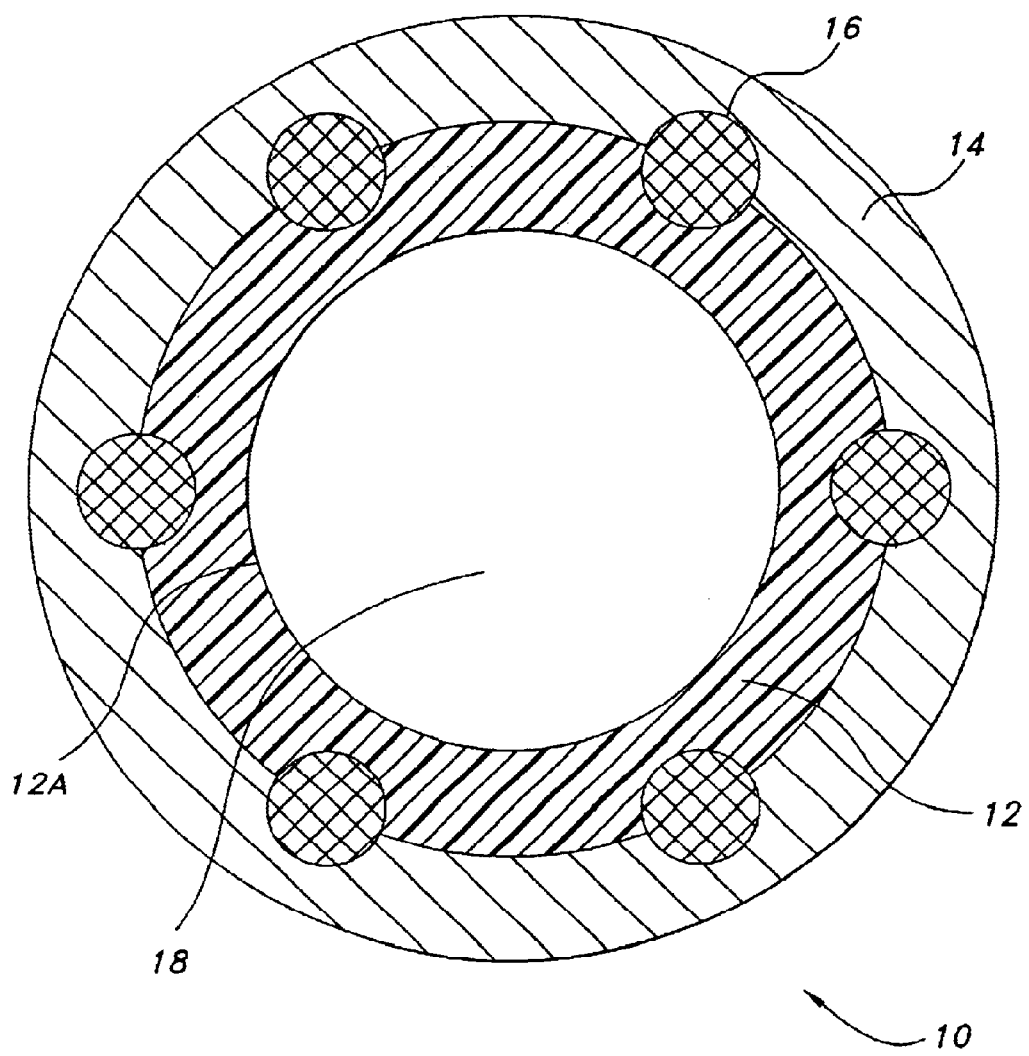
FIG. 1 is a cross-sectional showing of an embodiment of the present invention.

FIG. 1 shows a preferred embodiment of the present invention including a stent/graft composite device 10. Device 10 includes an inner tubular member 12 and an outer tubular member 14 disposed coaxially thereover. A central lumen 18 extends throughout tubular composite graft 10, defined further by the inner wall 12a of luminal tube 12, which permits the passage of blood through graft 10 once the graft is properly implanted in the vascular system.

An expandable stent 16 may be interposed between inner tubular member 12 and outer tubular member 14. Stent 16, which may be typically associated with the composite device, is used for increased support of the blood vessel and increased blood flow through the area of implantation. To this end, an increase in radial tensile strength at the outermost tube is important in that it enables the graft to support, for example, radial expansion of a stent.

As will be described in further detail hereinbelow, inner tubular member 12 and outer tubular member 14 have different porosities. One porosity is selected so as to provide enhanced strength, while the other porosity is selected to provide transport of bioactive agents therethrough.

Figure 2:
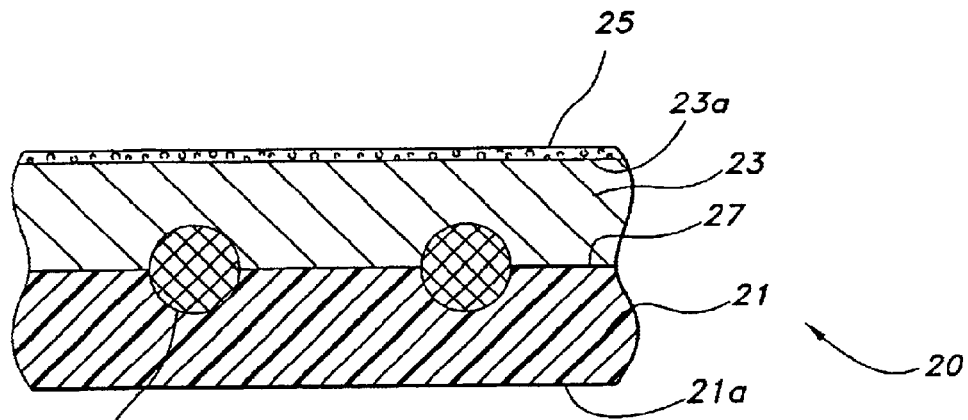
FIGS. 2–10 show schematic longitudinal cross-sectional representations of embodiments of the composite device of the present invention.
Figure 3:
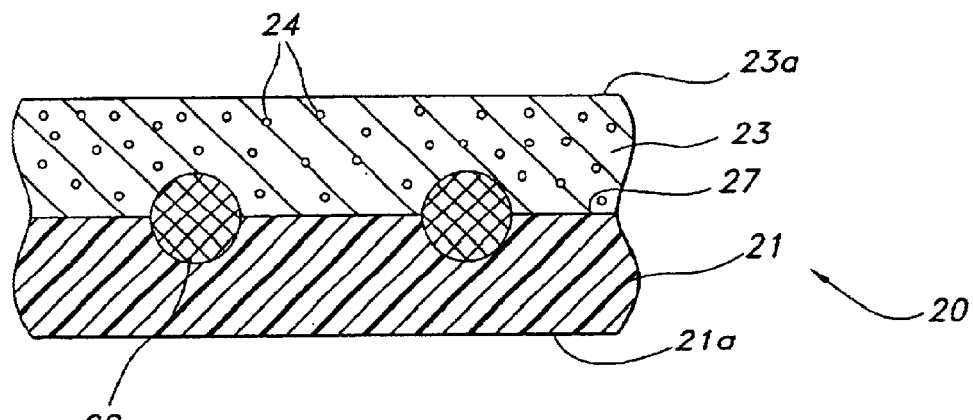
Figure 4:
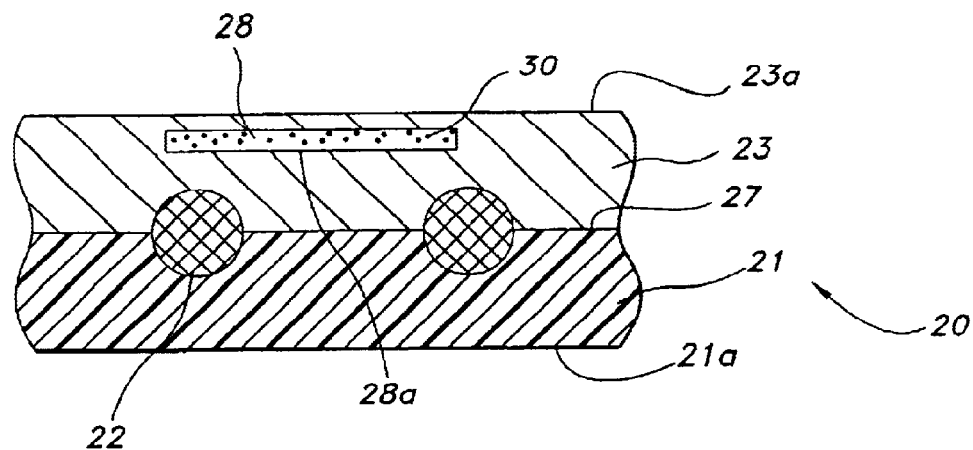

Referring now to FIGS. 2–4, the layers which define the composite prosthesis of the present invention may be more fully described. As noted above, the present invention takes the preferred embodiment of a composite tubular graft, wherein the layers shown in FIGS. 2–4 represent the tubular members forming the composite structure. However, it may be appreciated that the present invention also contemplates other implantable multi-layer prosthetic structures such as vascular patches, blood filters, film wraps for implantable devices such as stents, hernia repair fabrics and plugs and other such devices where such structures may be employed.

As shown in FIG. 2, the composite device 20 of the present invention includes a luminal zone 21 of first porosity and a second zone 23 of second porosity overlaying the luminal zone. The second zone permits regulated transport of bioactive agents 25 associated with the device therethrough. A distinct porosity change is clearly defined at the interface 27 between zones 21 and 23.

The luminal zone 21 is designed to have a relatively high IND, while the second zone 23 is designed to have a lower IND, as well as a higher density of fibrils. The luminal zone 21, having a higher IND, promotes enhanced endothelization along the inner blood contacting surface 21 a while the outer zone 23, having a lower IND, provides strength to the overall composite, by providing superior radial tensile and suture retention strengths and regulates delivery of bioactive agents 25 to the implantation site.

The composite device 20 exhibits a sharp porosity change at the interface 27 between the luminal zone 21 and second zone 23. This sharp porosity transition is preferably achieved by selecting luminal tube 21 to have generally a given uniform porosity therealong and then providing a selected second zone 23, disposed thereover as a tube or sheet, to have a resultant different porosity uniformly therealong. Thus, a distinct porosity change is exhibited on either side of the interface 27 defined between luminal zone 21 and outer zone 23. It is this distinct porosity change between the luminal zone 21 and second zone 23 which allows for the specific regulation and controlled delivery of bioactive agents 25 associated with the graft to the site of implantation.

Composite device 20 may further include stent 22 interposed between luminal zone 21 and outer zone 23. As described above, stents would be typically associated with tubular devices to provide increased support of the blood vessel following implantation.

Figure 5:
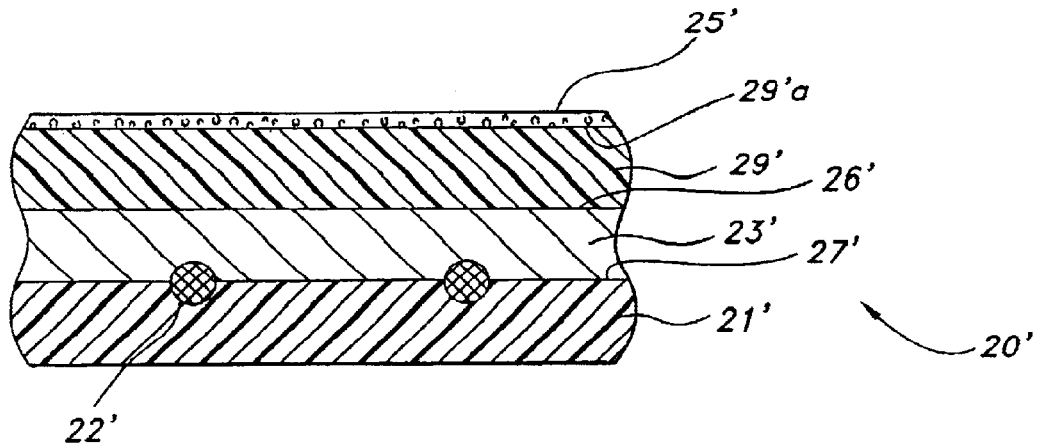

As will now be described, composite device 20 may further include a third porosity zone. For example, as shown in FIG. 5, a composite device 20' of the present invention may include a third zone 29' of third porosity overlaying the second zone 23'. The device 20' includes luminal zone 21' of first porosity and a second zone 23' of second porosity overlying luminal zone 21'. The second zone 23' permits the regulated transport of bioactive agents 25' associated with the device therethrough, and wherein a distinct change in porosity is exhibited at the interface 27' between luminal zone 21' and second zone 23'. The device further includes a third zone 29' of porosity overlying second zone 23' wherein a distinct change of porosity is exhibited at the interface 26' between zones 23' and 29'.

With regard to the three zone embodiment of FIG. 5, stent 22' is shown positioned between luminal zone 21' and second zone 23'. It is, however, contemplated that stent 21' may be patentably positioned between zones 23' and 29'.

One object of the present invention is to provide an implantable composite device for regulating delivery of bioactive agents associated therewith to a site of implantation of the device. For drug delivery, it is recognized that it is difficult to obtain constant drug delivery when administering the drug in the form of pills and injections. As a result of repeated doses, the drugs often cycle through concentration peaks and valleys, thus resulting in time periods of toxicity and ineffectiveness. Thus, localized drug delivery is desired.

The composite device of the present invention includes at least one bioactive agent which will be released from the device at a controlled rate in order to supply the bioactive agent where it is needed without the problems associated with systemic delivery.

The composite device of the present invention may achieve localized delivery of a bioactive agent to a site where it is needed in a number of ways. For example, as shown in FIGS. 2 and 5, the drug (25 and 25') may be coated on the outside surface (23a and 29a') of the graft. The drug may be applied to the outside surface of the graft such as by dipping, spraying, or painting.

Figure 6:
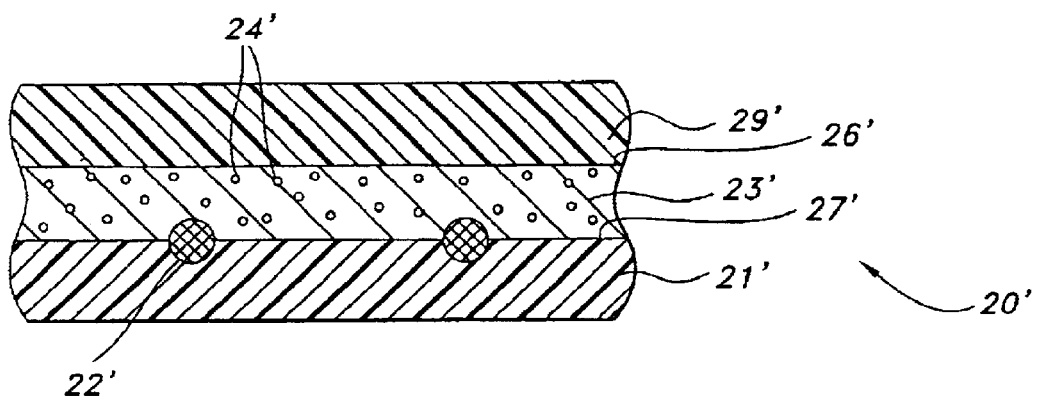
Figure 9:
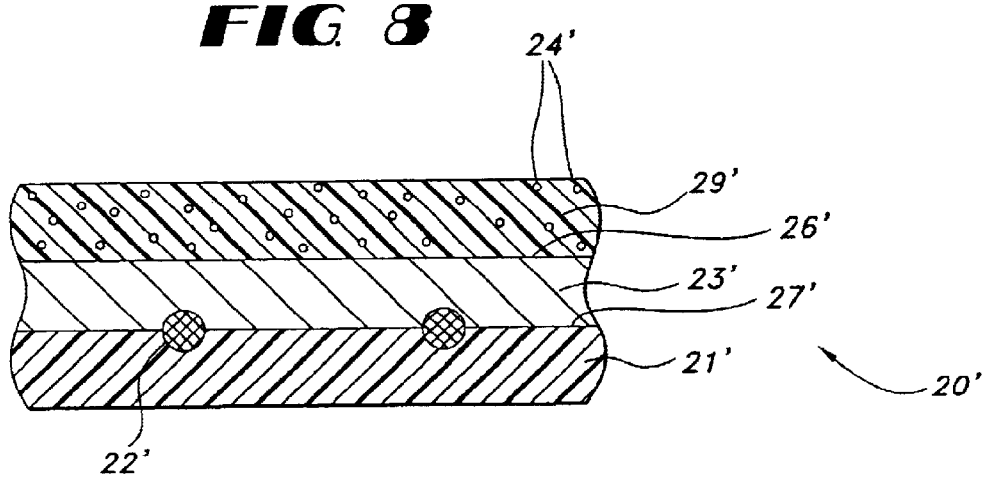

In a further embodiment, such as depicted in FIGS. 3 and 6, the drug (24 and 24') may be embedded in the second zone (23 and 23') of porosity. FIG. 6 depicts a preferred embodiment of the present invention. Alternatively, the third zone 29' may have a drug 24' embedded therein as shown in FIG. 9. In one example, the drug may be encapsulated in a polymer. The polymeric matrix containing the drug may include, without limitation, microparticles, microfibers or microfibrils. For example, a suitable microsphere for incorporation into the second layer would have a diameter of about 10 microns or less. The microsphere could be contained within the mesh of fine fibrils connecting the matrix of nodes in expanded polytetrafluoroethylene (ePTFE). The microparticles containing the drug may be incorporated within a zone by adhesively positioning them onto the polymeric material from which it is formed, for example, onto PTFE, or by mixing the microparticles with a fluid or gel and flowing them into the polymeric matrix of the second layer. The fluid or gel mixed with the microparticles could, for example, be a carrier agent designed to improve the cellular uptake of the bioactive agent incorporated into the composite device. Moreover, it is well within the contemplation of the present invention that carrier agents, which can include hyaluronic acid, may be incorporated within each of the embodiments of the present invention so as to enhance cellular uptake of the bioactive agent or agents associated with the device.

The microparticles embedded in the a zone may have a polymeric wall surrounding the drug or a matrix containing the drug and optional carrier agents. Due to the potential for varying thicknesses of the polymeric wall or matrix and for varying porosities and permeabilities of different polymeric materials suitable for containing a drug, there is provided the potential for an additional mechanism for controlling the release of a therapeutic agent in a highly regulated manner.

Moreover, microfibers or microfibrils, which may be drug loaded by extrusion, can be adhesively layered or woven into the polymeric material of a zone for drug delivery.

Figure 7:
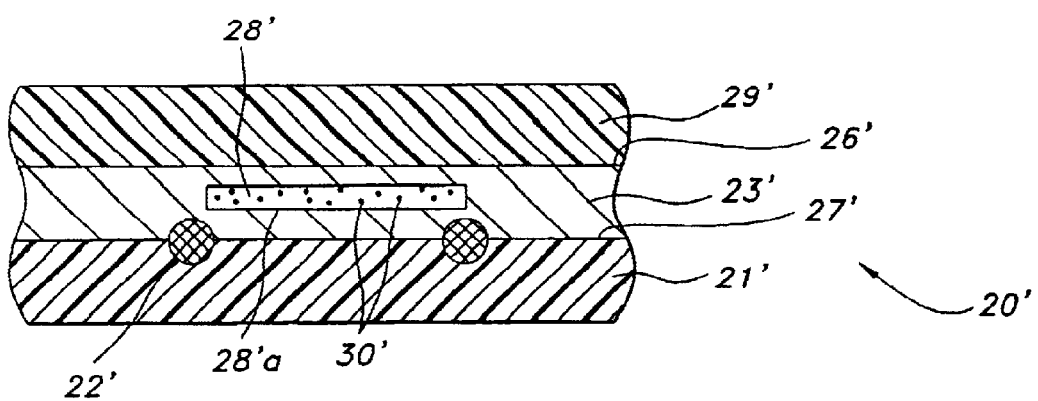
Figure 8:
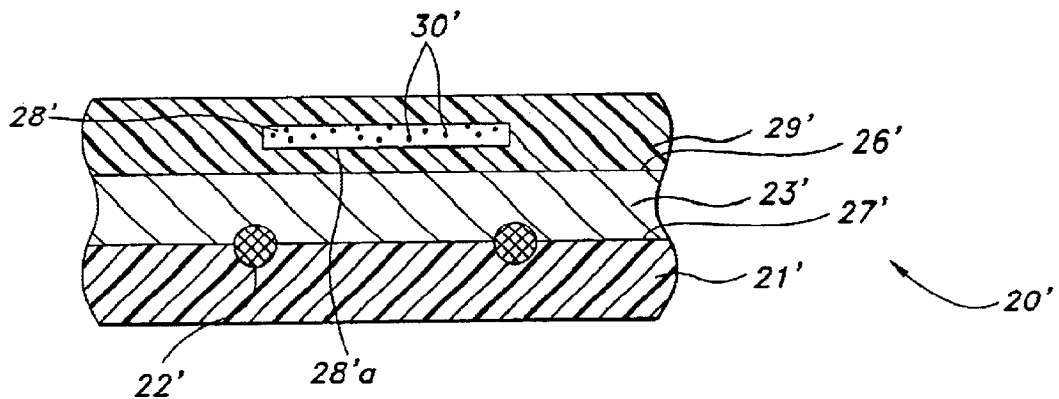

A further embodiment relating to drug delivery is shown in FIGS. 4 and 7 where the second zone (23 and 23') includes a reservoir (28 and 28') formed therein for containing a drug (30 and 30'). Alternatively, a reservoir may be included within the third zone of porosity 29' as shown in FIG. 8. With reference to FIG. 4, the outside wall 28a of reservoir 28 may be formed of a porous polymeric material which is sufficiently permeable to permit a bioactive agent disposed in the reservoir to diffuse through the reservoir wall 28a and into the polymeric material forming the second porosity zone 23. Subsequent diffusion of the bioactive material through the second zone of porosity permits regulated delivery of the bioactive agent to a site of implantation. Moreover, depending on the nature of the material used to form the outside wall of the reservoir, additional regulation of the flow and release of a bioactive agent to a needed site may be possible.

Figure 10:
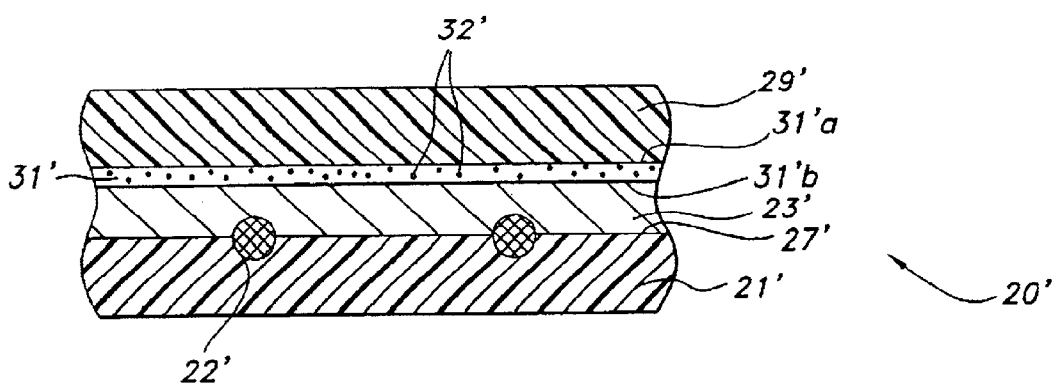

In yet another embodiment shown in FIG. 10, reservoir 31' for containing a bioactive agent is formed between the second 23' and third 29' zones. That is to say, the top wall 31a' of reservoir 31' has the porosity associated with third zone 29', whereas the bottom wall 31b' of reservoir 31' has a porosity the same as that of the second zone 23'. As such, passage of the bioactive agent 32' through bottom wall 31b' of reservoir 31' permits regulated passage and delivery of bioactive agent to the second zone 23'. Moreover, further diffusion of the bioactive agent through the porous matrix of the second zone, which acts as the layer regulating delivery of the bioactive agents, permits further and enhanced regulation of delivery of the agents to luminal zone 21' and to the lumen of the blood vessel where the agent or agents are needed.

The bioactive agents which achieve regulated and specific delivery through their association with the composite device of the present invention, may be selected from growth factors, anti-coagulant substances, stenosis inhibitors, thrombo-resistant agents, antibiotic agents, anti-tumor agents, anti-proliferative agents, growth hormones, antiviral agents, anti-angiogenic agents, angiogenic agents, anti-mitotic agents, anti-inflammatory agents, cell cycle regulating agents, genetic agents, cholesterol-lowering agents, vasodilating agents, agents that interfere with endogenous vasoactive mechanisms, hormones, their homologs, derivatives, fragments, pharmaceutical salts and combinations thereof.

Cells that have been genetically engineered to deliver bioactive proteins, such as the above-mentioned growth factors or antibodies, to the implant site may be associated with the composite device of the present invention. Cells can be of human origin (autologous or allogeneic) or from an animal source (xenogeneic). The delivery media can be formulated as needed to maintain cell function and viability. A suitable means of delivery of genetically-engineered cells to the implantation site may be by use of a reservoir, such as that shown in FIGS. 4 and 7.

Thrombo-resistant agents associated with the composite device may be selected from the following agents: heparin, heparin sulfate, hirudin, hyaluronic acid, chondroitin sulfate, dermatan sulfate, keratan sulfate, PPack (dextrophenylalanine proline arginine chloromethylketone), lytic agents, including urokinase and streptokinase their homologs, analogs, fragments, derivatives and pharmaceutical salts thereof Anti-coagulants may be selected from the following: D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors, tick antiplatelet peptides and combinations thereof Suitable antibiotic agents may be selected from the group consisting of penicillins, cephalosporins, vancomycins, aminoglycosides, quinolones, polymyxins, erythromycins, tetracyclines, chloramphenicols, clindamycins, lincomycins, sulfonamides their homologs, analogs, derivatives, pharmaceutical salts and combinations thereof Anti-proliferative agents for use in the present invention include, but are not limited to the following: enoxaprin, angiopeptin, or monoclonal antibodies capable of blocking smooth muscle cell proliferation, hirudin, acetylsalicylic acid, and combinations thereof.

Useful vascular cell growth inhibitors include, but are not limited to, the following: growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin.

Suitable vascular cell growth promoters include, but are not limited to, transcriptional activators and transcriptional promoters.

Useful anti-tumor agents for use in the present invention include, but are not limited to, paclitaxel, docetaxel, alkylating agents including mechlorethamine, chlorambucil, cyclophosphamide, melphalan and ifosfamide, antimetabolites including methotrexate, 6-mercaptopurine, 5-fluorouracil and cytarabine, plant alkaloids including vinblastine, vincristine and etoposide, antibiotics including doxorubicin, daunomycin, bleomycin, and mitomycin, nitrosureas including carmustine and lomustine, inorganic ions including cisplatin, biological response modifiers including interferon, angiostatin agents and endostatin agents, enzymes including asparaginase, and hormones including tamoxifen and flutamide their homologs, analogs, fragments, derivatives, pharmaceutical salts and combinations thereof Furthermore, anti-viral agents include, but are not limited to, amantadines, rimantadines, ribavirins, idoxuridines, vidarabines, trifluridines, acyclovirs, ganciclovirs, zidovudines, foscarnets, interferons their homologs, analogs, fragments, derivatives, pharmaceutical salts and mixtures thereof.

Useful anti-inflammatory agents include agents such as: dexamethasone, prednisolone, corticosterone, budesonide, estrogen, sulfasalazine, mesalamine, and combinations thereof.

In one desired embodiment, an anti-mitotic agent may be a radioactive material coupled to a biologically compatible carrier. In particular, the radioactive material may be selected from alpha-particle emitting isotopes and beta-particle emitting isotopes. Useful beta-particle emitting isotopes for treatment are generally selected from $^{32}P$, $^{131}I$, $^{90}Y$ and mixtures thereof.

In other embodiments, the bioactive agent associated with the composite device of the present invention may be a genetic agent. Examples of genetic agents include DNA, anti-sense DNA, and anti-sense RNA. DNA encoding one of the following may be particularly useful in association with an implantable device according to the present invention: (a) tRNA or rRNA to replace defective or deficient endogenous molecules; (b) angiogenic factors including growth factors such as acidic and basic fibroblast growth factors, vascular endothelial growth factor, epidermal growth factor, transforming growth factor $\alpha$ and $\beta$, platelet-derived endothelial growth factor, platelet-derived growth factor, tumor necrosis factor $\alpha$, hepatocyte growth factor and insulin-like growth factor; (c) cell cycle inhibitors; (d) thymidine kinase and other agents useful for interfering with cell proliferation; and (e) the family of bone morphogenic proteins. Moreover DNA encoding for molecules capable of inducing an upstream or downstream effect of a bone morphogenic protein may be useful.

The second zone of porosity is desired to be formed from a synthetic polymer, natural polymer, or a combination thereof. Synthetic polymers may include, but are not limited to, ePTFE, polyurethanes, polyacrylamides, polyvinyl alcohols, polyphosphate esters, polyethersulfone, polyorthoesters, polyesters, siloxane polymers, silicones, polyvinylpyrrolidone, polyvinyl ethers, polyethers, polycarbonate, polyalkylenes, polyamides, polyanhydrides, polyethylene oxides, polyvinyl aromatics, polyhydroxybutyrate valerate, polyhydroxybutyrate-co-hydroxyvalerate, polyacrylic acid, polyhydroxybutyrate valerate, polyhydroxybutyrate-co-hydroxyvalerate, polyacrylic acid and derivatives and mixtures thereof. Moreover, the natural polymer is desired to be selected from the group consisting of fibrin, elastin, celluloses, collagen, gelatin, vitronectin, fibronectin, laminin, reconstituted basement membrane matrices, starches, dextrans, alginates, hyaluronic acid, polylactic acid, polyglycolic acid, polypeptides, glycosaminoglycans, their derivatives and mixtures thereof.

In one embodiment, the natural and synthetic polymers forming the second zone in a composite device are biostable or bioabsorbable polymers. Wherein the composite device is biostable, the bioactive agent may diffuse out from the biostable material in which it is incorporated, for example. If, however, the polymer used to form the second layer is bioabsorbable, a bioactive agent incorporated therein may be delivered to a site where it is needed in part by the process of degradation and resorbtion of the polymer itself While biological polymeric materials such as fibrin, collagen, and elastin possess high biocompatability per se, their mechanical properties are often inadequate and, furthermore, they cost much more to produce than synthetic polymers. Therefore, synthetic and biological polymers may be combined in order to produce a device having the superior mechanical properties associated with a synthetic component and the biocompatability associated with a biological component. Moreover, the blending of synthetic and biological polymers offers increased flexibility in terms of the porosity and permeability of the resultant combined blend for increased ability to affect in a specific way the size of the bioactive agent capable of diffusing through the layer and the delivery rate thereof to the site of implantation. Blending techniques are well known such as those described in the International Journal of Artificial Organs, Vol. 14, No. 5, 1991, pp 295–303.

A further aspect of the second zone of the present composite device is that it is capable of modulating the penetration of cells such as endothelial cells between the luminal zone and the third zone, when present. Moreover, the presence of the second zone provides increase strength to the overall composite.

The porosity of the second zone may be designed to achieve desirable properties in the structure and geometry of the nodes and fibrils that affect permeability and prevent tissue in-growth. In one desired embodiment, the second zone is a layer formed of ePTFE having pores of an internodal distance from about 5 to about 10 microns. In a further embodiment, the second layer of ePTFE has a specific node/fibril geometry of about 5 to about 10 microns. Furthermore, it is important that the fibril density of the second layer is sufficient to regulate the delivery of a drug.

It is a further aspect of the devices of this invention having three zones of porosity that the porosities of the luminal and third zones are designed to increase radial and suture retention strengths of the composite device, as well as promote enhanced cell endothelization, preferably along the inner luminal surface of the graft. In one desired embodiment, the third zone exhibits a radial strength in excess of the radial strength of the luminal zone. For example, in this case, the third zone has pores of an internodal distance of less than 40 microns, whereas the luminal zone of ePTFE has pores of an internodal distance of greater than 40 microns. The larger IND associated with the luminal layer is designed to enhance cell endothelization along the luminal surface as the graft is inherently more porous and this contributes to long term healing and patency of the graft. The decrease in the porosity of the third zone, relative to luminal zone, results in an increase in the overall radial tensile strength of the device, as well as an increase in the ability for the graft to retain a suture placed therein during implantation.

It is an additional object of the present invention where three porosity zones are present to provide a composite device wherein the luminal zone exhibits a radial strength in excess of the radial strength of the third zone. In this instance, the third zone provides a porosity sufficient to promote enhanced cell growth and tissue incorporation, hence more rapid healing, and the inner luminal zone has a high degree of strength. In one embodiment, the first luminal layer of ePTFE has pores of an internodal distance of less than 40 microns and the third layer of ePTFE has pores of an internodal distance of greater than 40 microns.

The composite device according to the present invention may be formed by adheringly supporting tubular structures over one another to form a composite tubular graft as described in further detail below. Moreover, the method may further include interposing an implantable prosthetic stent between the layers and/or incorporating a bioactive agent into the device.

It is within the contemplation of the present invention that the bioactive agent may be incorporated within or onto the composite structure of this invention either prior to, during, or following implantation. For example, wherein the drug is to be contained within a reservoir, the reservoir may be incorporated within the structure of the device during the method of making and, following implantation, the drug can be delivered to the reservoir by use of a mini-pump which can be attached to the reservoir of the device, for example, by a catheter. Alternatively, the drug may be added to the reservoir prior to implantation of the device, such as by pre-filling the reservoir with a syringe.

Specifically, the composite device of the present invention may be formed by expanding a thin wall PTFE inner luminal tube at a relatively high degree of elongation, on the order of approximately between 400 and 2,000% elongation and preferably from about between 700% and 900%. The inner luminal tube is expanded over a cylindrical mandrel, such as a stainless steel mandrel at a temperature of between room temperature and 645° F., preferably about 500° F. The luminal tube is preferably, but not necessarily fully sintered after expansion. Sintering is typically accomplished at a temperature of between 645° F. and 800° F., preferably at about 660° F. and for a time of between about 5 minutes to 30 minutes, preferably about 15 minutes. The combination of the luminal ePTFE tube over the mandrel is then employed as a substrate over which the second layer, corresponding to the drug regulating layer in the form of a tube or sheet, is expanded. The interior diameter of the second tube is selected so that it may be easily but tightly disposed over the outside diameter of the inner luminal tube. The composite structure formed between the two tubes is then sintered at preferably similar parameters.

As described above, a drug may be incorporated within the second layer during the method of making which is described in further detail below. In one example, the drug is incorporated into a suitable microparticle which is either adhesively positioned onto the polymeric material forming the second layer, or by mixing the microparticles with a fluid or gel and flowing them into the polymeric matrix of the second layer. Alternatively, the drug may be coated on the outside surface of the second layer by such methods as dipping, spraying or painting. Moreover, a reservoir for drug delivery may be incorporated into the second layer during its method of making and, following implantation, the drug can be delivered to the reservoir by use of a minipump which can be attached to the reservoir of the device, for example, by a catheter. Alternatively, the drug may be added to the reservoir prior to implantation of the device, such as by pre-filling the reservoir with a syringe. Furthermore, a bioactive agent or drug can be incorporated into the polymeric material of the second layer during the method of making the second layer in the following manner: mixing into an extrudate used to make a second layer formed of ePTFE, a crystalline, particulate material like salt or sugar that is not soluble in a solvent used to form the extrudate; casting the extrudate solution with particulate material into a thin film or sheet; and then applying a second solvent, such as water, to dissolve and remove the particulate material, thereby leaving a porous sheet. The porous sheet may then be placed into a solution containing a bioactive agent in order to fill the pores. Preferably, a vacuum would be pulled on the sheet to insure that the bioactive agent applied to the sheet is received into the pores.

With reference to the methods and conditions under which the second layer is formed, as with the known methods of processing PTFE, the method for preparing the second layer of ePTFE utilizes a preformed billet which includes a PTFE resin mixed with an organic solvent. It is noted that extrusion conditions have a large effect on an extrudate's reaction to being stretched. For example, extrudate qualities may be controlled by a number of factors including the amount of organic solvent mixed with the resin to form a billet, the reduction ratio at which the billet is extruded and the extrusion rate. Each of these is believed to influence the micromechanical properties of the extruded article.

A billet which has a solvent level of about 10 to 30% by weight yields an extrudate suitable for the stretching process necessary to produce the drug regulating layer. Moreover, it is desired that the preformed billet is extruded to a reduction ratio of about 200 to 1. An additional parameter which has a significant effect on the resulting extrudate property upon being stretched is the extrusion pressure. Suitable extrusion pressures to practice the present invention include pressures of about 5,000 PSI to about 10,000 PSI.

With further reference to the making of the drug regulating layer, once an extrudate has been produced, it is stretched under conditions capable of yielding a layer which is uniform over a large portion of its length. Stretching conditions are given in terms of stretch rate and stretch ratio. Stretch rate refers to the percentage change in length of the extrudate per unit time. It is desired for the drug regulating layer that the stretch rate correspond to about 7 to about 8 inches per second. The percentage change is calculated with reference to the starting length of the extrudate. In contrast, stretch ratio is not time dependent but refers to the ratio of the final length of the stretched extrudate to that of the initial length of the unstretched extrudate. With respect to the drug regulating layer, it is desired that the stretch ratio be about 2.5 to 1. Moreover, it is desired that a temperature of about 250° C. be maintained during the process of stretching and that the extrudate is placed in tension during the stretching process.

After the extrudate corresponding to the drug regulating layer has been stretched, it is desired to be is sintered by heating it above its crystalline melting point while under tension. This allows the microstructure of the material to be set properly and completes the process of producing the drug regulating layer. The expansion and sintering of the second tube, corresponding to the drug regulating area, over the inner luminal tube serves to adheringly bond the interface between two tubes, resulting in a single composite structure.

Wherein the device according to the present invention is to include an optional third layer, the combination of the composite formed between luminal tube and second tube is then employed as a substrate, over which the third tube is expanded. The level of elongation of the third tube is lower than that of the inner luminal tube in a desired embodiment, approximately between 200% and 500% elongation and preferably about 400%. As before, the expansion and sintering of the outermost third tube over the second tube serves to adheringly bond the interface between these two tubes, resulting in another composite structure provided by this invention. The resulting composite structure formed by the method described above would desirably have an inner surface, defined by an inner luminal tube, which exhibits an IND of greater than 40 microns, and in particular between 40 and 100 microns, spanned by a moderate number of fibrils.

Such a microporous structure is sufficiently large so as to promote enhanced cell endothelization once blood flow is established through the graft. Such cell endothelization enhances the long term patency of the graft.

The outer structure of a device containing a third tube formed by the method described above has a smaller microporous structure, with an IND of less than 40 microns and desirably 15–35 microns and a substantial fibril density. This IND results in an increase in the strength of the outermost tube, and enhances the composite structure. Importantly, the outer surface defined by the outermost tube exhibits enhanced suture retention due to the smaller IND.

The middle structure, defined by second tube, has an even smaller microporous structure, with and IND of between 5–10 microns and a fibril density sufficient to provide regulated and specific delivery of small molecules, such as drugs, which are associated with the implantable device to a site of treatment, such as the lumen of a blood vessel.

The forming process, as described above, results in a bonded interface between the luminal tube and second tube. A further bonded interface is formed between the second tube and the third tube, when present. These interfaces exhibit sufficient interfacial strength resulting from the direct sintering of the tubes over one another to assure complete bonding of the tubes. The strength of the interfaces between the tubes may be independently varied through a selection of processing conditions and relative dimensions of precursor extruded tubes as desired to yield a range of performance. The following examples serve to provide further appreciation of the invention, but are not meant in any way to restrict the scope of the invention.

EXAMPLES

Example 1

Figure 11:
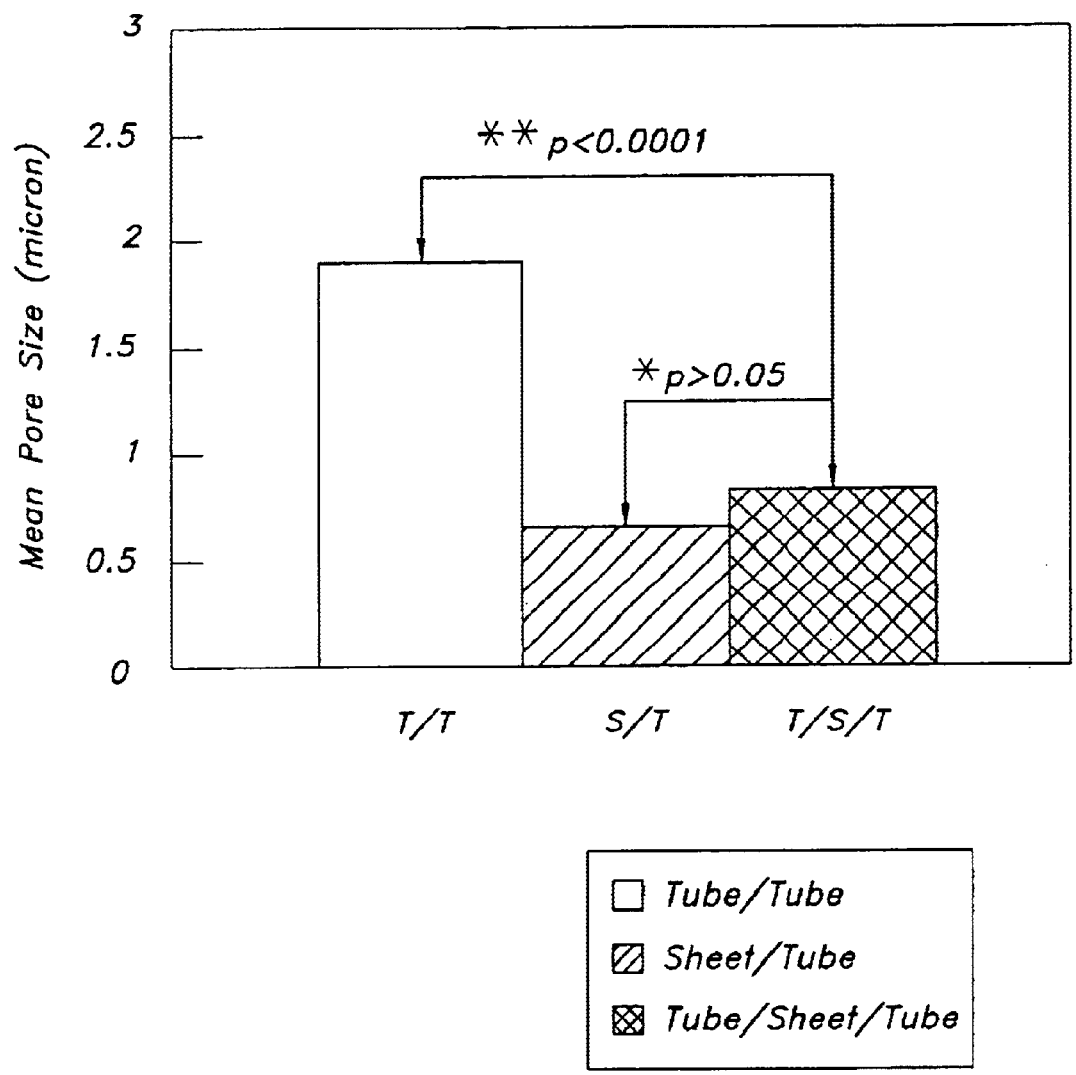
FIG. 11 is a graphical representation of mean pore sizes obtained from two embodiments of an endovascular graft according to the present invention and a comparative example.

In Example 1, several ePTFE coverings were constructed and tested for porosity. These results are shown in the graph in FIG. 11. In FIG. 11, T/T, S/T and T/S/T represent the comparative example, a first embodiment of the invention and a second embodiment of the invention respectively.

Comparative Example

In FIG. 11, the Tube/Tube (T/T) refers to an endovascular graft (EVG) with the following construction:

Outside layer: ePTFE graft with 20–30 µm internodal distance

Inside layer: ePTFE graft with 40–60 µm internodal distance

First Embodiment

The Sheet/Tube (S/T) refers to an endovascular graft (EVG) with the following construction:

Outside layer: ePTFE graft/sheet with 5–10 µm internodal distance

Inside layer: ePTFE graft with 40–60 µm internodal distance

Second Embodiment

The Tube/Sheet/Tube (T/S/T) refers to an endovascular graft (EVG) with the following construction:

Outside layer: ePTFE graft with 20–30 µm internodal distance

Middle layer: ePTFE graft/sheet with 5–10 µm internodal distance

Inside layer: ePTFE graft with 40–60 μm internodal distance

Third Embodiment

Outside layer: ePTFE graft with 20–30 μm internodal distance

Middle layer: ePTFE graft with 5–10 μm internodal distance

Inside layer: ePTFE graft with 40–60 μm internodal distance

The results analyzed by unpaired t-test. Probability values (P) less than 0.05 were considered to be significance only.

Example 1 provides three separate embodiments containing a drug regulating layer according to the present invention. A comparative example is included which does not contain a drug-regulating layer. Various inside, middle and outside layers of ePTFE were constructed. Certain layers were made from extruded tube and others made from extruded sheet ePTFE material. Combinations of the tubes and sheets are indicated above. As evidenced from the separate embodiments, the internodal distances of the outer, middle where present, and inside layers differed. In the first embodiment, the outside layer shown serves as the drug regulating layer. In both the second and third embodiment, the middle layer shown serves as the drug regulating area.

As shown in the graph in FIG. 11, the mean pore sizes of the first (S/T) and second (T/S/T) embodiments of the ePTFE covering of the invention are approximately 50% less than that of the comparative example, indicating the coverings of the composite devices of the invention provide the capacity for regulated transport of bioactive agents through the devices.

A first embodiment was made using a sheet/tube construction having a stent placed therebetween. This embodiment is represented in FIG. 1, which shows either tubes or sheets being used on the inner and/or outer stent graft. The outside layer is formed from an ePTFE sheet having an internodal distance of about 5 to about 10 microns internodal distance. The outside layer was constructed of an ePTFE tubular graft having an internodal distance of about 40 to about 60 microns. The outside sheet layer serves as the bioactive regulating layer and contained the bioactive agent within the pores of the ePTFE. Impregnation of this ePTFE layer with the bioactive agent was performed in some instances prior to lamination, using pressurized methods, and in other instances, subsequent to lamination of the composite stent graft device. In instances where the lamination was performed subsequent to impregnation of the outer regulating layer with bioactive material, care was given to the precise temperature conditions necessary to perform the lamination function, without deleteriously effecting the ability of the bioactive agent to perform its intended functions.

Alternatively, the drug regulating layer in the first embodiment was prepared by immersing the ePTFE tube or sheet in a liquid medium containing the bioactive agent. Ultimately, a liquid coating of the bioactive agent was applied to the tube sheet, either prior to lamination with the inside ePTFE layer or subsequent to lamination of the two layers.

The second embodiment shown in this example relates to a three layer composite stent graft device having the bioactive regulating layer as a middle layer. The outside layer of the device is an ePTFE tube having an internodal distance of about 20 to about 30 microns. The middle layer, which regulates the transport of bioactive material, is made from an ePTFE sheet having an internodal distance of about 5 to about 10 microns and the inside luminal layer of the stent graft device is made from an ePTFE extruded tube having an internodal distance of about 40 to about 60 microns. In some samples, the middle layer was coated and/or impregnated with the bioactive material prior to its lamination to the inside luminal layer. In other samples, the impregnation or coating occurred subsequent to lamination. As an alternative sample, the middle and outside layers were laminated together prior to lamination with the inside layer. The middle layer in this instance was also coated and/or impregnated with the bioactive material, in some instances prior to lamination with the outside layer, as well as other instances where it was impregnated and/or coated subsequent to lamination with the outer layer. In the latter instance, the drug could be coated or forced into the interstices of the expanded inside surface of the middle layer prior to joining and laminating with the inner layer of the composite stent graft device.

A third embodiment was made substantially the same as the second embodiment above, with the exception of all three ePTFE layers were formed from extruded tubes.

In both the second and third embodiments mentioned above, the stent was positioned relative to the three layers between the inside and middle layers of the stent graft device. Alternatively, however, the stent could also be positioned between the middle and outside layers of the stent graft device.

What is claimed is:

1. An implantable composite device for regulating delivery of a bioactive agent associated therewith to a site of implantation of said device comprising: (a) said bioactive agent; (b) a first luminal layer comprising ePTFE and having a first porosity sufficient to promote cell endothelization therealong; (c) a second polymeric layer disposed over said first layer, said second layer having a second porosity permitting regulated transport of said bioactive agents therethrough; and (d) a third layer disposed over said second polymeric layer, said third layer comprising ePTFE and having a third porosity, and said third layer exhibiting a radial strength in excess of the radial strength of said first layer.

2. The composite device of claim 1, wherein said second layer has said bioactive agent embedded therein.

3. The composite device of claim 1, wherein said second layer has said bioactive agent coated thereon.

4. The composite device of claim 1, wherein said second layer includes a reservoir containing said bioactive agent.

5. The composite device of claim 1, wherein said third layer has said bioactive agent embedded therein.

6. The composite device of claim 1, wherein said third layer has said bioactive agent coated thereon.

7. The composite device of claim 1, wherein said third layer includes a reservoir formed therein containing said bioactive agent.

8. The composite device of claim 1, further including a reservoir between said second and third layers containing said bioactive agent.

9. The composite device of claim 1 wherein said device is a tubular member.

10. The composite device of claim 1, wherein said second layer comprises ePTFE having pores of an internodal distance from about 5 to about 10 microns.

11. The composite device of claim 10, wherein said second layer has a specific node/fibril geometry of about 5 to about 10 microns.

12. The composite device of claim 1, wherein said first layer has pores of an internodal distance of greater than 40 microns and said third layer has pores of an internodal distance of less than 40 microns.

13. The composite device of claim 1, further comprising an implantable prosthetic stent between said first and said second layers.

14. The composite device of claim 1, further comprising an implantable prosthetic stent between said second and said third layers.

15. The composite device of claim 1, wherein said second layer is selected from the group consisting of synthetic polymer, natural polymer or a combination thereof.

16. The composite device of claim 15, wherein said synthetic polymer is selected from the group consisting ePTFE, polyurethanes, polyacrylamides, polyvinyl alcohols, polyphosphate esters, polyethersulfone, polyorthoesters, polyesters, siloxane polymers, silicones, polyvinylpyrrolidone, polyvinyl ethers, polyethers, polycarbonate, polyalkylenes, polyamides, polyanhydrides, polyethylene oxides, polyvinyl aromatics, polyhydroxybutyrate valerate, polyhydroxybutyrate-co-hydroxyvalerate, polyacrylic acid and derivatives and mixtures thereof.

17. The composite device of claim 15, wherein said natural polymer is selected from the group consisting of fibrin, elastin, celluloses, collagen, gelatin, vitronectin, fibronectin, laminin, reconstituted basement membrane matrices, starches, dextrans, alginates, hyaluronic acid, polylactic acid, polyglycolic acid, polypeptides, glycosaminoglycans, their derivatives and mixtures thereof.

18. The composite device of claim 15, wherein said natural polymer and said synthetic polymer are biostable or bioabsorbable polymers.

19. The composite device of claim 1, wherein said bioactive agent is selected from the group consisting of growth factors, anti-coagulant substances, stenosis inhibitors, thrombo-resistant agents, antibiotic agents, anti-tumor agents, anti-proliferative agents, growth hormones, antiviral agents, anti-angiogenic agents, angiogenic agents, anti-mitotic agents, anti-inflammatory agents, cell cycle regulating agents, genetic agents, cholesterol-lowering agents, vasodilating agents, agents that interfere with endogenous vasoactive mechanisms, hormones, their homologs, derivatives, fragments, pharmaceutical salts and combinations thereof.

20. An implantable composite device for regulating delivery of a bioactive agent associated therewith to a site of implantation of said device comprising: (a) said bioactive agent; (b) a first luminal layer comprising ePTFE and having pores of an internodal distance of greater than 40 microns; and (c) a second layer comprising ePTFE disposed over said first layer, said second layer having pores of an internodal distance from about 5 to about 10 microns and a specific node/fibril geometry of about 5 to about 10 microns, the second layer permitting regulated transport of natural or synthetic bioactive agents therethrough, and (d) a third layer disposed over said second layer, said third layer comprising ePTFE and having a third porosity.

21. The implantable composite device of claim 20, wherein said second layer further includes a natural polymer selected from the group consisting of fibrin, elastin, celluloses, collagen, gelatin, vitronectin, fibronectin, laminin, reconstituted basement membrane matrices, starches, dextrans, alginates, hyaluronic acid, polylactic acid, polyglycolic acid, polypeptides, glycosaminoglycans, their derivatives and mixtures thereof.

22. The implantable composite device of claim 20, wherein said bioactive agent is selected from the group consisting of growth factors, anti-coagulant substances, stenosis inhibitors, thrombo-resistant agents, antibiotic agents, anti-tumor agents, anti-proliferative agents, growth hormones, antiviral agents, anti-angiogenic agents, angiogenic agents, anti-mitotic agents, anti-inflammatory agents, cell cycle regulating agents, genetic agents, cholesterol-lowering agents, vasodilating agents, agents that interfere with endogenous vasoactive mechanisms, hormones, their homologs, derivatives, fragments, pharmaceutical salts and combinations thereof.

23. The composite device of claim 20 further comprising an implantable prosthetic stent between said first and said second layers.

24. An implantable composite device for regulating delivery of a bioactive agent associated therewith to a site of implantation of said device comprising: (a) said bioactive agent; (b) a first luminal layer comprising ePTFE and having pores of an internodal distance of greater than 40 microns; and (c) a second layer comprising ePTFE disposed over said first layer, said second layer having pores of an internodal distance from about 5 to about 10 microns and a specific node/fibril geometry of about 5 to about 10 microns, the second layer permitting regulated transport of natural or synthetic bioactive agents therethrough, and (d) a third layer disposed over said second layer, said third layer comprising ePTFE and having pores of an internodal distance of less than 40 microns.

25. The composite device of claim 24 further comprising an implantable prosthetic stent between said second and said third layers.

26. The composite device of claim 24 further comprising an implantable prosthetic stent between said first and said second layers.

27. An implantable composite device for regulating delivery of a bioactive agent to a site of implantation of said device comprising: (a) a bioactive agent; (b) a first luminal layer of first porosity, (c) a second layer comprising ePTFE disposed over said first layer, said second layer having pores of an internodal distance from about 5 to about 10 microns and a specific node/fibril geometry of about 5 to about 10 microns, the second layer permitting regulated transport of natural or synthetic bioactive agents therethrough; and (d) a third layer comprising ePTFE and having pores of an internodal distance of less than 40 microns disposed over said second layer.

28. The implantable composite device of claim 27, wherein said second layer further includes a natural polymer selected from the group consisting of fibrin, elastin, celluloses, collagen, gelatin, vitronectin, fibronectin, laminin, reconstituted basement membrane matrices, starches, dextrans, alginates, hyaluronic acid, polylactic acid, polyglycolic acid, polypeptides, glycosaminoglycans, their derivatives and mixtures thereof.

29. The implantable composite device of claim 27, wherein said bioactive agent is selected from the group consisting of growth factors, anti-coagulant substances, stenosis inhibitors, thrombo-resistant agents, antibiotic agents, anti-tumor agents, anti-proliferative agents, growth hormones, antiviral agents, anti-angiogenic agents, angiogenic agents, anti-mitotic agents, anti-inflammatory agents, cell cycle regulating agents, genetic agents, cholesterol-lowering agents, vasodilating agents, agents that interfere with endogenous vasoactive mechanisms, hormones, their homologs, derivatives, fragments, pharmaceutical salts and combinations thereof.

30. The composite device of claim 27 further comprising an implantable prosthetic stent between said first and said second layers.

31. The composite device of claim 27 further comprising an implantable prosthetic stent between said second and said third layers.

32. A method of making an implantable composite device for regulating delivery of a bioactive agent associated therewith to a site of implantation of said device, said method comprising: (a) providing a device structure comprising a second polymeric layer having a second porosity disposed between (i) a first luminal layer comprising ePTFE and having a first porosity sufficient to promote cell endothelization therealong and (ii) a third layer comprising ePTFE material and having a third porosity, said third layer exhibiting a radial strength in excess of the radial strength of said first layer; and (b) disposing said bioactive agent within said device structure, said second layer permitting regulated transport of said bioactive agent therethrough.

33. The method of claim 32, further comprising interposing an implantable prosthetic stent between said first and said second layers.

34. The method of claim 32, further comprising interposing an implantable prosthetic stent between said second and said third layers.

35. The method of claim 32, wherein said second layer has said bioactive agent embedded therein.

36. The method of claim 32, wherein said second layer has said bioactive agent coated thereon.

37. The method of claim 32, wherein said second layer includes a reservoir containing said bioactive agent.

38. The method of claim 32, wherein said third layer has said bioactive agent embedded therein.

39. The method of claim 32, wherein said third layer has said bioactive agent coated thereon.

40. The method of claim 32, wherein said third layer includes a reservoir formed therein containing said bioactive agent.

41. The method of claim 32, wherein said device includes a reservoir between said second and third layers containing said bioactive agent.

42. The method of claim 32, wherein said second layer comprises ePTFE having pores of an internodal distance from about 5 to about 10 microns.

43. The method of claim 42, wherein said second layer has a specific node/fibril geometry of about 5 to about 10 microns.

44. The method of claim 32, wherein said first luminal layer of ePTFE has pores of an internodal distance of greater than 40 microns and said third layer of ePTFE has pores of an internodal distance of less than 40 microns.

45. The method of claim 32, wherein said second layer is selected from the group consisting of synthetic polymer, natural polymer or a combination thereof.

46. The method of claim 45, wherein said synthetic polymer is selected from the group consisting of ePTFE, polyurethane, polyacrylamide, polyvinyl alcohol, polyphosphate ester, polyhydroxybutyrate valerate, polyhydroxybutyrate-co-hydroxyvalerate, polyacrylic acid, polyethersulfone, polyorthoesters, polyesters, siloxane polymers, silicones, polyvinylpyrrolidone, polyvinyl ethers, polyethers, polycarbonate, polyalkylenes, polyamides, polyanhydrides, polyethylene oxides, polyvinyl aromatics, polyhydroxybutyrate valerate, polyhydroxybutyrate-cohydroxyvalerate, polyacrylic acid and derivatives and mixtures thereof.

47. The method of claim 45, wherein said natural polymer is selected from the group consisting of fibrin, elastin, celluloses, collagen, gelatin, vitronectin, fibronectin, laminin, reconstituted basement membrane matrices, starches, dextrans, alginates, hyaluronic acid, polylactic acid, polyglycolic acid, polypeptides, glycosaminoglycans, their derivatives and mixtures thereof.

48. The method of claim 45, wherein said natural polymer and said synthetic polymer are biostable or bioabsorbable polymers.

49. The method of claim 32, wherein said bioactive agent is selected from the group consisting of growth factors, anti-coagulant substances, stenosis inhibitors, thrombo-resistant agents, antibiotic agents, anti-tumor agents, anti-proliferative agents, growth hormones, antiviral agents, anti-angiogenic agents, angiogenic agents, anti-mitotic agents, anti-inflammatory agents, cell cycle regulating agents, genetic agents, cholesterol-lowering agents, vasodilating agents, agents that interfere with endogenous vasoactive mechanisms, hormones, their homologs, derivatives, fragments, pharmaceutical salts and combinations thereof.

* * * * *